(12) United States Patent
Steinberg

(10) Patent No.: US 7,232,415 B2
(45) Date of Patent: Jun. 19, 2007

(54) SYSTEM AND METHOD FOR NONINVASIVELY EVALUATING A LIMB SUSPECTED OF COMPARTMENT SYNDROME

(75) Inventor: Bruce Steinberg, Jacksonville, FL (US)

(73) Assignee: NCSE, LLC, Jacksonville, FL (US)

( * ) Notice: Subject to any disclaimer, the term of this patent is extended or adjusted under 35 U.S.C. 154(b) by 0 days.

(21) Appl. No.: 11/453,292

(22) Filed: Jun. 14, 2006

(65) Prior Publication Data

US 2007/0028929 A1 Feb. 8, 2007

Related U.S. Application Data

(63) Continuation-in-part of application No. 10/730,482, filed on Dec. 8, 2003, now Pat. No. 7,097,625, which is a continuation-in-part of application No. 10/038,040, filed on Oct. 19, 2001, now Pat. No. 6,659,967.

(51) Int. Cl.
  *A61B 5/103* (2006.01)
  *A61B 5/00* (2006.01)
  *A61B 5/03* (2006.01)
  *G01N 3/48* (2006.01)

(52) U.S. Cl. .......................... 600/587; 600/561; 73/81

(58) Field of Classification Search ................ 600/488, 600/561, 587, 592, 595; 73/81, 573
See application file for complete search history.

(56) References Cited

U.S. PATENT DOCUMENTS

| | | | | |
|---|---|---|---|---|
| 3,680,386 A | * | 8/1972 | Cannon | 600/587 |
| 4,159,640 A | * | 7/1979 | Leveque et al. | 73/81 |
| 4,245,496 A | | 1/1981 | Napetschnig et al. | |
| 4,739,769 A | * | 4/1988 | Matthews et al. | 600/486 |
| 4,817,629 A | * | 4/1989 | Davis et al. | 600/561 |
| 5,038,795 A | * | 8/1991 | Roush et al. | 600/587 |

(Continued)

FOREIGN PATENT DOCUMENTS

DE 43 43 612 A1 6/1995

(Continued)

OTHER PUBLICATIONS

Ostrander and Lee, "Testing Viscoelastic Properties of Biological Soft Tissue", VA Medical Center, Castle Point, NY 12511, pp. 107-109.

(Continued)

*Primary Examiner*—Charles A. Marmor, II
*Assistant Examiner*—Christine D. Hopkins
(74) *Attorney, Agent, or Firm*—Holland & Knight LLP

(57) ABSTRACT

A system and method are disclosed for noninvasively diagnosing limb compartment syndrome by measuring a quantitative modulus of hardness. In the preferred embodiment, a nonmovable pressure probe mounted in the center of a movable spring loaded platform is applied against a limb compartment. Force is gradually applied to the probe and the platform, compressing a limb compartment. Pressure on the probe is measured as the probe pushes into the limb. The spring loaded platform displaces, and the distance of the probe tip to the platform is measured. This distance is the depth of compression into the limb by the probe. The relationship of incremental pressures in the probe and the corresponding distance of the probe tip to the platform for each pressure is plotted. A linear regression analysis is performed whose slope forms a quantitative modulus of hardness.

10 Claims, 11 Drawing Sheets

U.S. PATENT DOCUMENTS

| | | | |
|---|---|---|---|
| 5,224,469 A * | 7/1993 | Mocny | 601/108 |
| 5,564,435 A * | 10/1996 | Steinberg | 600/561 |
| 5,879,312 A * | 3/1999 | Imoto | 600/587 |
| 6,063,044 A * | 5/2000 | Leonard et al. | 600/587 |
| 6,186,962 B1 * | 2/2001 | Lloyd et al. | 600/587 |
| 6,659,967 B1 * | 12/2003 | Steinberg | 600/587 |
| 7,097,625 B2 * | 8/2006 | Steinberg | 600/587 |

FOREIGN PATENT DOCUMENTS

| | | |
|---|---|---|
| EP | 0420287 | 4/1991 |
| WO | WO 01/26232 A | 4/2001 |

OTHER PUBLICATIONS

Joseph, "Measurement of tissue hardness: can this be a method of diagnosing compartment syndrome noninvasively in children?" Journal of Pediatric Orthop. B 2006, pp. 443-448.

Dickson, et. al., "Noninvasive Measurement of Compartment Syndrome", Ortho Blue Journal, Dec. 2003, vol. 26, No. 12, pp. 1215-1218.

* cited by examiner

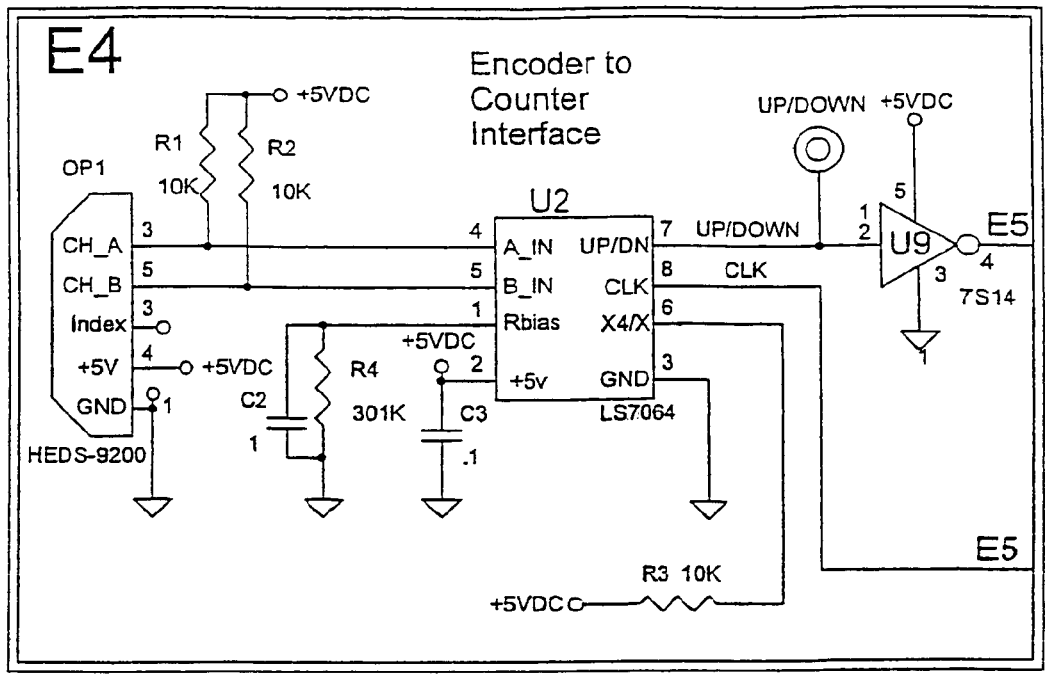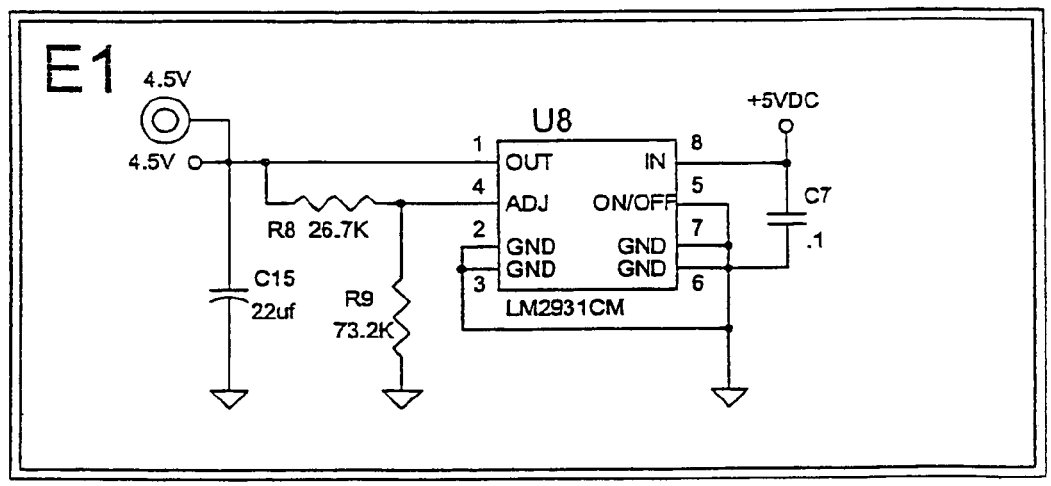
*FIG. 4*

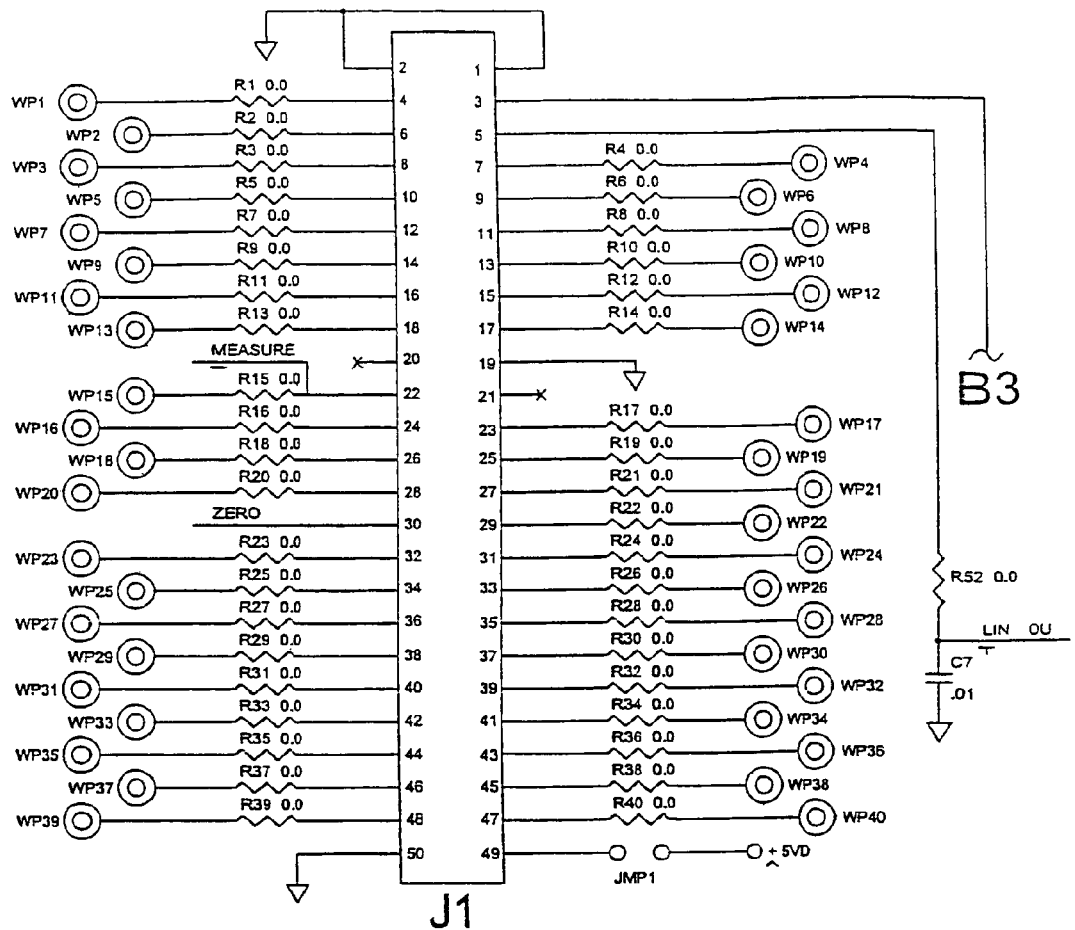
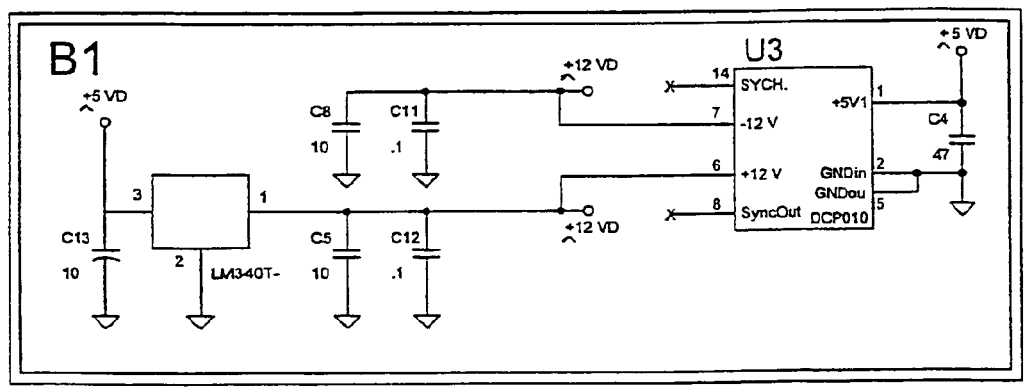
FIG. 5

SYSTEM AND METHOD FOR NONINVASIVELY EVALUATING A LIMB SUSPECTED OF COMPARTMENT SYNDROME

CROSS REFERENCES TO RELATED APPLICATIONS

This application is a Continuation-In-Part of commonly owned U.S. patent application Ser. No. 10/730,482, filed Dec. 8, 2003, now U.S. Pat. No. 7,097,625 which is a Continuation-In-Part of U.S. patent application Ser. No. 10/038,040. filed Oct. 19, 2001, now U.S. Pat. No. 6,659,967. Both of these related applications are fully incorporated herein by reference.

BACKGROUND OF THE INVENTION

1. Field of the Invention

This invention pertains to the measurement of hardness of the tissue of a limb by using a noninvasive technique. More specifically, the present invention relates to a warning device that safeguards against the development of compartment syndrome by relating harness to intracompartmental interstitial pressure.

2. Description of the Background Art

The diagnosis of compartment syndrome is made by the direct measurement of intracompartmental interstitial pressure based on a technique developed by Dr. Thomas E. Whitesides, Jr. In this technique, a small amount of fluid is injected into a limb compartment. The pressure necessary to advance the fluid into the compartment is the measurement of the pressure of the compartment. If the intracompartmental interstitial pressure should increase to within 30 mmHg of the diastolic pressure, this could result in irreversible damage of the tissue within the compartment. Treatment for such a condition is emergency surgical release of the fascia overlying the muscle, which is constricting the compartment. Delay in the diagnosis of compartment syndrome and subsequently delay in performing the fasciotomy can result in the needless loss of function, contracture and possible amputation of the limb.

The decision to perform a fasciotomy for a suspected compartment syndrome is frequently difficult. In the classic article by Dr. Thomas E. Whitesides, Jr., "Tissue Pressure Measurements as a Determinant of the Need for Fasciotomy", Clin. Orthop., 113:43, 1975, even if physicians are well versed in the signs and symptoms of compartment syndrome, the clinical analysis sometimes is indefinite and confusing, resulting in delay in performing the fasciotomy.

According to Dr. Whitesides Jr., the one factor that must be present in a compartment syndrome is increased intracompartmental interstitial pressure. Therefore, the effectiveness of the fasciotomy is based on relieving this pressure and re-establishing tissue perfusion. In order to effectively diagnose compartment syndrome, a technique for measuring tissue pressure has been established. For details of the technique of direct intracompartmental interstitial pressure measurement, refer to the article cited above by Dr. Thomas E. Whitesides, Jr.

Compartment syndrome occurs in skeletal muscles enclosed by osseofascial boundaries. The condition develops when accumulating fluid creates high interstitial pressure within a closed osseofascial space, reducing perfusion of surrounding tissues below a level necessary for viability. As the interstitial pressure within the compartment increases, the expansion of the compartment is limited by the compliance of the osseofascial envelope. Like a balloon about to burst, the envelope becomes less and less compliant as the interstitial pressure increases. The change in compliance can be detected by palpation.

Dr. Bruce Steinberg is the inventor of the device described in U.S. Pat. No. 5,564,435. That device quantitatively measures palpation, linear regression of force applied to volume displaced, and has shown a correlation between quantitative modulus of hardness and the interstitial pressure within a compartment. Dr. Steinberg et al. in an article "Evaluation of Limb Compartments with Suspected Increased Interstitial Pressure", Clin. Ortho. No. 300, p 248–253, 1994, demonstrates how such a device can be used to assess compartment pressure with quantitative hardness measurements. Dr. Steinberg, however, has found that this particular device is cumbersome because of its difficulty in application. The device must be applied to a limb with a continuous stable force while a piston mounted within the platform moves to compress the limb. Measurements become inaccurate if there is any movement of the limb or the device. In the setting of a painful limb in trauma, this measurement becomes very difficult because the patient has difficulty maintaining the limb still. The device described by Dr. Steinberg in U.S. Pat. No. 5,564,435 requires that two separate forces be applied simultaneously, the continuous stable force for the force plate and a second force to increase the pressure within the piston. The measurements that derive the hardness result from the piston. As the pressure increases and as the piston compresses the limb compartment, measurements of pressure and displacement are simultaneously recorded while the device is held stable against the limb at a known force plate pressure.

The present invention overcomes this complexity by applying only one force to obtain the measurement of both pressure and displacement. This is done by mounting a stable pressure measuring probe where the piston was previously located. In addition, instead of having the platform as stable and nonmovable, the platform is now spring loaded and moves as pressure is applied to the limb. In effect, the probe pushes against the limb and the platform or force plate moves as the probe forces itself into the limb. The displacement of the probe is now measured by the distance between the probe tip and the movable platform. When removed from the limb, the spring loaded platform realigns to an even level with the probe tip (the spring force is slightly greater than the weight of the platform). In this way, the measurement of pressure within the probe is obtained electronically and the distance between the tip of the probe and the platform is measured as well electronically. A quantitative hardness can be obtained by the relationship between probe pressure and platform displacement. This quantitative measurement of palpation can then be used to assess the interstitial pressure within a compartment. This is a significant improvement over the prior art in that one can now apply a device to the limb with one hand and not worry about the difficulty of maintaining a constant force against the limb with one hand, while then pressurizing the piston mounted within the platform with the other hand. Dr. Steinberg has found with the new device application is faster

SUMMARY OF THE INVENTION

It is therefore one of the objectives of this invention to provide a system for noninvasively evaluating a limb suspected of compartment syndrome.

It is also an object of the present invention to evaluate a limb by measuring and recording simultaneous pressure and distance values.

It is a further object of the present invention to make a medical diagnosis on the basis of recorded pressure and distance values.

These and others objects of the present invention are achieved via a noninvasive technique which monitors the condition of limb tissue. More particularly, a noninvasive technique is disclosed for diagnosing and monitoring compartment syndrome. In the preferred embodiment of the invention, a pressure measuring probe is mounted within a spring loaded platform, where the platform is movable and distance is measured relative to the probe. Using this device, one may obtain measurements to assess the hardness of a limb compartment. More particularly, the preferred embodiment of the invention includes an apparatus and method for evaluating the condition of tissue within a limb. The method comprises of the following steps. First applying the apparatus to a limb with a force of application. Second, as this force is increased the change in the pressure of the mounted probe is recorded while the distance that the probe moves into the limb is recorded by the movement of a platform also applied against the limb. The method also includes the step of determining the relationship of multiple points of pressure within the probe to the distance the probe to the compression measured, formulating a quantitative harness curve. Additionally, this invention also includes a linear regression analysis of the multiple points of the curve to determine a quantitative harness modulus.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

The present invention relates to a system and method for noninvasively evaluating a limb for compartment syndrome. The system utilizes a force applicator instrument which is applied to a limb suspected of having the syndrome. The instrument includes a spring biased force plate which is mounted about a probe. This plate is displaced as the instrument is employed in applying an increasing force to the limb. The pressure applied to the probe is detected and recorded, as is the displacement of the force plate relative to the force probe. Linear regression techniques are applied to the pressure and distance data to compute hardness of the limb. A compartment syndrome diagnosis is then made in accordance with the hardness computation. Details of the system and method are elaborated upon more fully hereinafter.

System of the Present Invention

Figure 1:
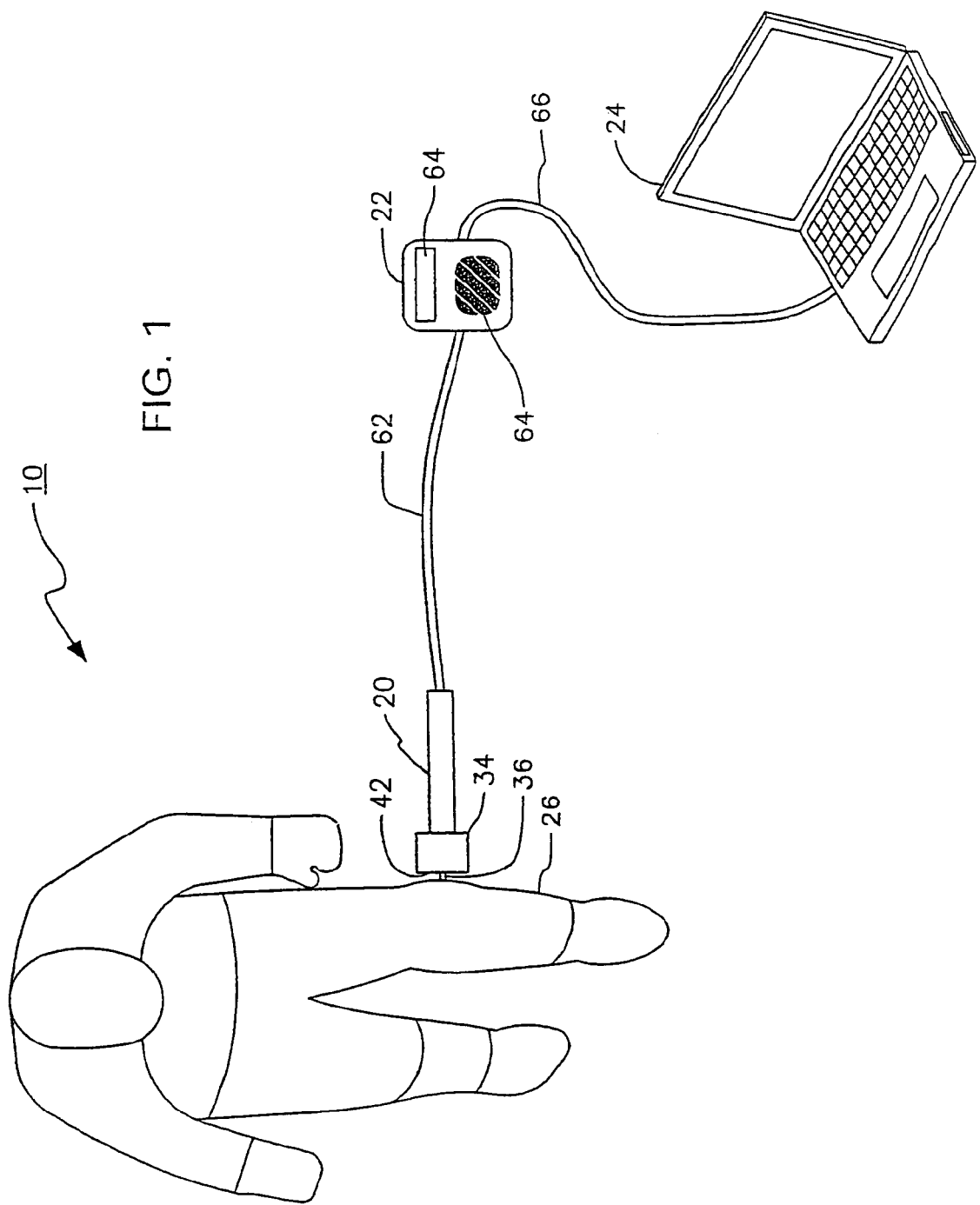
FIG. 1 is a schematic overview of the system of the present invention.
Figure 2:
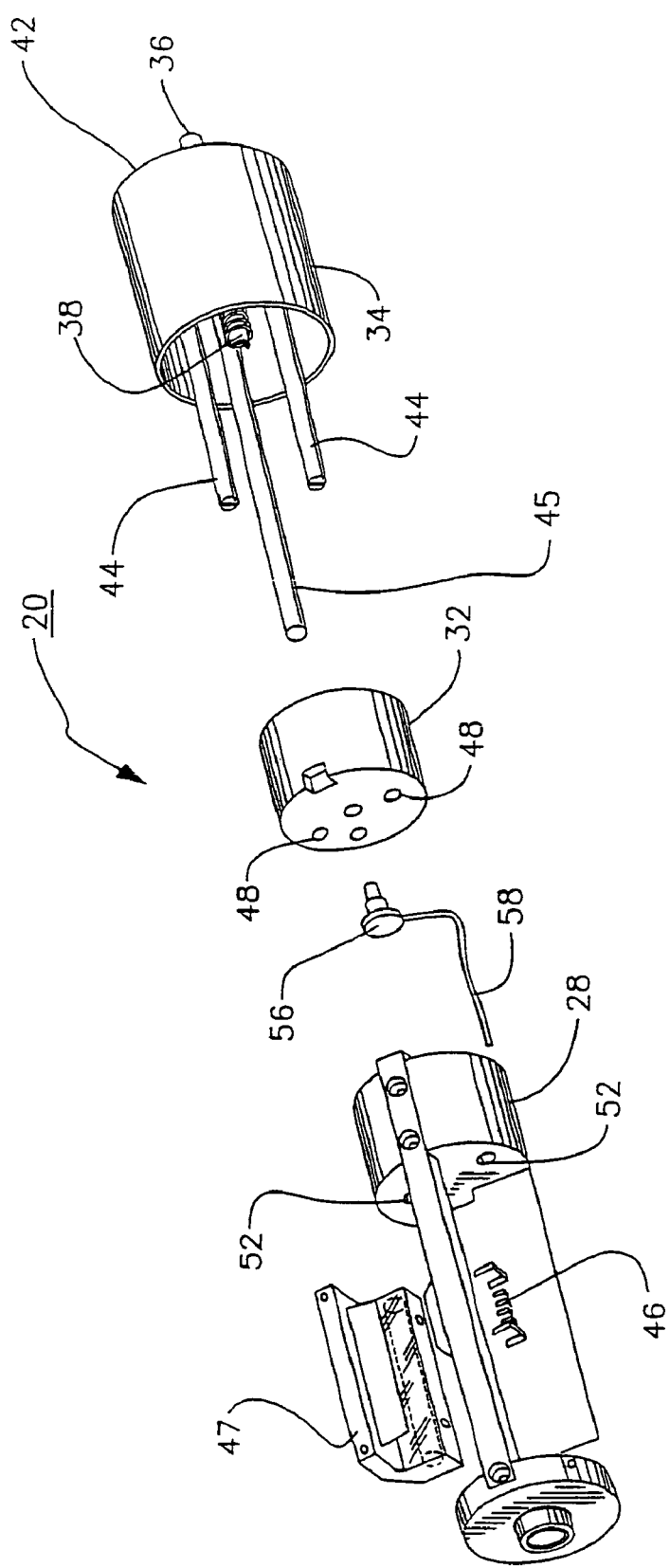
FIG. 2 is an exploded view of the force applicator employed in the system in the present invention.
Figure 3:
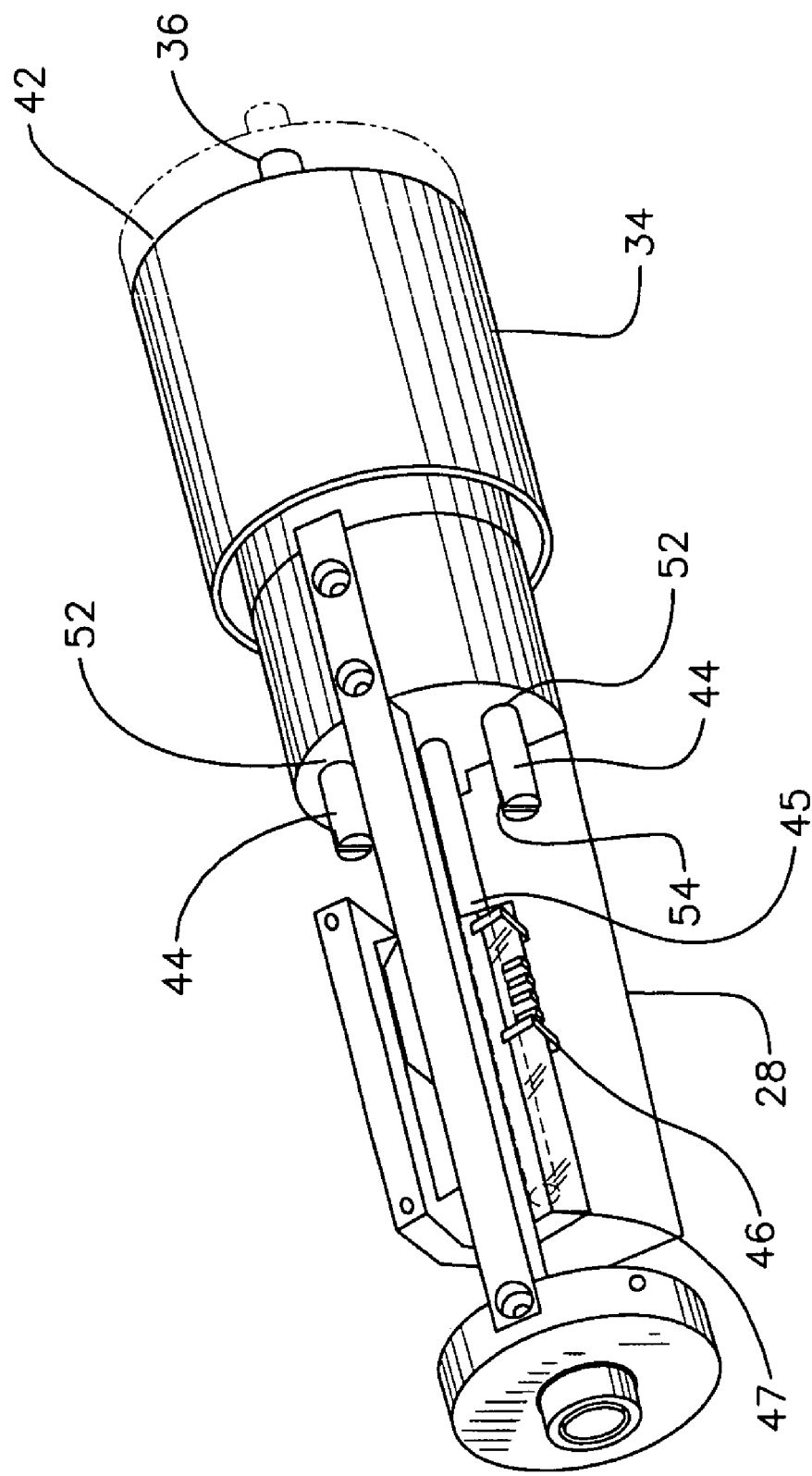
FIG. 3 is an assembled view of the force applicator of the present invention

With reference now to FIG. 1, the system 10 of the present invention is depicted. The system 10 employs an applicator instrument 20, a break out box 22 and a computer 24. Applicator instrument 20 is preferably a hand held device employed by the doctor in applying pressure to a limb 26 of a patient. With reference to FIG. 2, the various components of instrument 20 are depicted in an exploded view. These include: a base portion 28, a housing portion 32, a force plate 34, and a force probe 36. Force probe 36 is preferably positioned through a central aperture within force plate 34. A spring 38 serves to interconnect force probe 36 and force plate 34. More specifically, a helical spring is wound about the end of probe 36 positioned within force plate 34. This connection results in probe 36 and plate 34 being biased with respect to one another. That is, force plate 34 is permitted to slide relative to the probe 36 against the bias of the spring tension. Ideally, the spring tension is selected such that the distal end of probe 36 is flush with the outer face of the force plate 34 with spring 38 in an unbiased state. Thus, prior to the instrument 20 being applied to the limb 26 of a patient, the distal end 42 of instrument 20 presents a relatively flat surface. Thereafter, as the instrument 20 is driven into a limb 26 the force plate 34 is caused to slide rearwardly to expose force probe 36.

With continuing reference to FIG. 2, the stabilizing columns 44 and 45 of force plate 34 are depicted. More specifically, two shorter columns 44 and one elongated column 45 are included. These columns 44 and 45 move linearly within corresponding apertures formed within the housing and base portions (48 and 52, respectively). These columns 44 and 45 are mounted to the interior of force plate 34 and function in guiding the plate 34 as it passes rearwardly over house and base portions (32 and 28, respectively).

Base portion 28 includes an encoder 46 that is employed in measuring the travel distance of elongated stabilizing column 45. Specifically, column 45 is received within apertures formed within housing portion 32, base portion 28, and within an elongated cylindrical aperture formed in L-shaped bracket 47. A portion of bracket 47 is translucent. Encoder 46 includes Light Emitting Diodes (LEDS) and both transmit and detect light. Consequently, light transmitted through the translucent portion of bracket 47 can detect the presence or absence of column 45. In this manner, the position of the end of column 45 within bracket 47 can be detected by encoder 46. This distance measurement corresponds to the travel of force plate 34 relative to force probe 36. This distance measurement is recorded and used in future calculations, as described more fully hereinafter.

A centrally located load cell 56 is interconnected to force probe 36 for use in measuring the pressure applied to force probe 36. This load cell 56 is interconnected to the opposite end of force probe 36 and is positioned intermediate housing portion 32 and base position 28. Specifically, probe 36 extends through the central aperture of housing portion 32 and contacts load cell 56. A lead 58 is included for passing signals from cell 56 to breakout box 22. As such, pressure applied to probe 36 is transmitted to the load cell 56 where it is measured and recorded. Additionally, force probe 36 and load cell 56 are fixed with respect to the remainder of instrument 20. Consequently, the force applied to instrument 20 by the operator is transferred to both force probe 36 and the limb region 26.

The system thus described is employed in sensing and measuring both pressure and distance values. The pressure values reflect the pressure encountered by force probe 36 as instrument 20 is pressed into a limb 26. The distance measurement reflects the distance between force plate 34 and probe 36 which occurs as instrument 20 is pressed into a limb 26. The components of the system employed in utilizing and analyzing this data are described next.

With reference to FIG. 1 the breakout box 22 of the system 10 is depicted. Box 22 is electrically coupled to applicator instrument 20 by suitable cabling 62. The breakout box 22 functions in receiving pressure measurements from the load cell 56. These values are then compared against preset set minimum and maximum values. When the minimum pressure is met an indicator means 64 within box 22 signals the start of the data sampling period. That is, simultaneous pressure and distance values are recorded for a predetermined length of time only after a threshold pressure value is met. In the preferred embodiment, the threshold pressure value is 25 grams. Reaching this value starts the data acquisition cycle within computer 24, the user is also alerted to the initiation of the cycle by indicator means 64. In the preferred embodiment the sampling time is 3 seconds. Indicator 64 provides audible beeps during the acquisition cycle, preferably one beep per second. Likewise, if the doctor applies too much pressure with instrument 20 the indicator means provides a warning signal. In the preferred embodiment, the maximum pressure is between 7.5–10 lbs. The indicator means 64 can take the form of a audible beep or can be carried out by way of a visual monitor.

The computer 24 is also electrically coupled to the breakout box by suitable cabling 66. This computer 24 preferably takes the form of a laptop or desktop computer. However, the computer can also take the form of a specialized data processor specifically adapted for carrying out the present invention. Whatever the form, computer 24 is used in providing electrical power to instrument 20 as well as breakout box 22. Furthermore, computer 24 is employed in collecting, storing, and analyzing the pressure and distance measurements collected by the applicator instrument 20. Once stored within computer 24, the data is analyzed and employed in making diagnostic assessments.

Method of the Present Invention

The inventive method carried out by the system of the present invention is next described. In accordance with the method, the applicator is used by a doctor to apply increasing pressure to a limb region suspected of compartment syndrome. This increasing pressure is applied over a predetermined time period by the distal end of the applicator instrument.

In the next step of the method, the pressure applied to the force probe is repeatedly sensed and measured. These values are then stored over the predetermined time period.

In a similar fashion, the distance between the force plate and force probe at the distal end of the instrument is measured and stored. Again, this measurement is repeatedly taken over the course of a predetermined time period.

The distance and pressure values are then plotted as a curve. An analysis of the curve is then carried out by linear regression techniques to determine a limb hardness. In a final step of the method, a medial diagnosis is made on the basis of the computed hardness.

Handpiece Electronics

The handpiece schematic (FIG. 4) discloses the electronics within the handheld applicator instrument. DC power is supplied by the laptop computer 5 volt bus. A regulated 4.5VDC is created by circuitry E1 (FIG. 4)—a National Semiconductor chip (LM2931CM) to power the load cell. This output voltage powers the force probe load cell FIG. 4, circuitry E3 (Entran Part # ELFM-B1-10L, Fairfield, N.J.) and FIG. 2. When force is applied to the handheld applicator instrument, the force signal from the probe E3 (FIG. 4) is converted to an analog signal in circuit E2 (FIG. 4) and output to connector cable J1 position 2. Within circuitry E2 (FIG. 4) the load cell is wired to J2 and instrumentation amplifier U7 (INA114AU—BurrBrown, Tucson, Ariz.) converts the differential input from the force probe to a calibrated analog output. An output of 10 volts corresponds to the maximum force reading of 10 pounds. This pressure signal goes through connector cable J1 to the breakout box.

Breakout Box Electronics

The breakout box (FIG. 5) performs several functions, as described hereinafter. The box allows an interface from a 50 conductor flat computer cable to a durable small diameter handpiece cable.

Figure 5A:
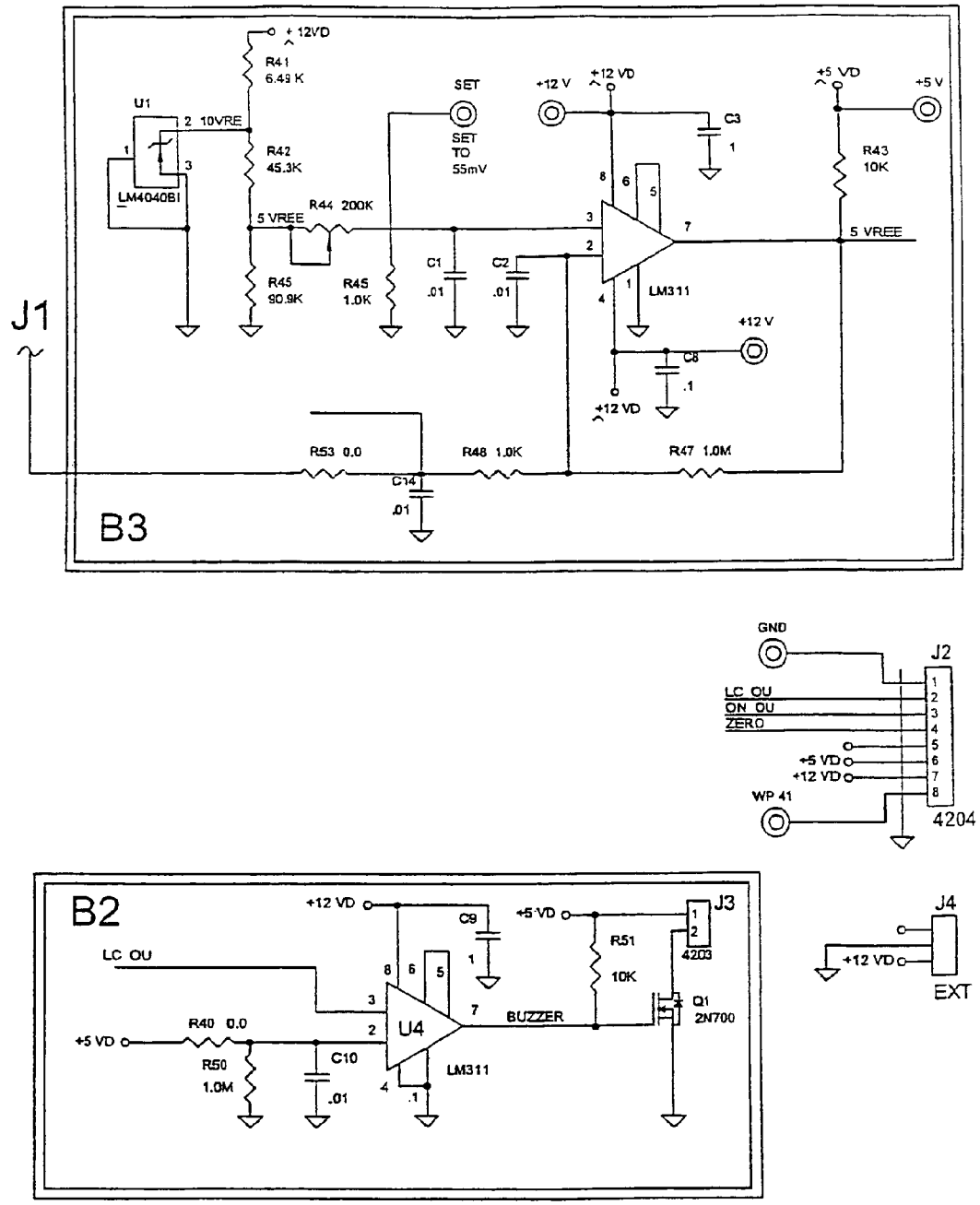
FIG. 5 is an electronic schematic of the breakout box of the system of present invention.

FIG. 5 circuitry B1 also utilizes +5VDC laptop bus and U3 (DCP0105 Burr-Brown Tucson, Ariz.) to create a ±12 VDC supply for analog IC requirements; FIG. 5 circuitry B2 comparator U4 (LM311 National Semiconductor) detects when ten pounds of force is present on load cell, and sounds an alarm to alert the operator (i.e. doctor) that the maximum load cell pressure is being applied.

FIG. 5 circuitry B3 comparator U2 provides a "MEASURE" signal when load cell pressure reaches 25 grams which zeroes the Data Acquisition Card (DAC) in the handpiece and triggers the laptop to begin data acquisition. A 50 conductor flex cable interfaces with the laptop through a data acquisition card (DAQ700) and DAQ software from National Instruments (Lab View).

The displacement of the force plate (FIG. 2) occurs as progressive force is applied to the handheld instrument pushing probe into the limb. Force plate is normally maintained flush with the tip of probe by a spring that maintains a constant force slightly greater than the weight of force plate. (This force is essentially constant regardless of the position of force plate.) This spring (partially shown in FIG. 2) is installed around probe. The force plate has three attached columns that stabilize and direct the displacement of the force plate through the housing of the instrument. As the elongated column (FIG. 2) moves through the housing, optical encoder (USDigital—Vancouver, Wash.) of FIG. 4 circuitry E4 and FIG. 2 generates a series of pulses which are fed to U2, a quadrature decoder interface IC (LS7064

USDigital—Vancouver, Wash.). Signals from U2, (UP/DOWN* directional signal and CLK distance signal) feed into circuitry E5.

Figure 4A:
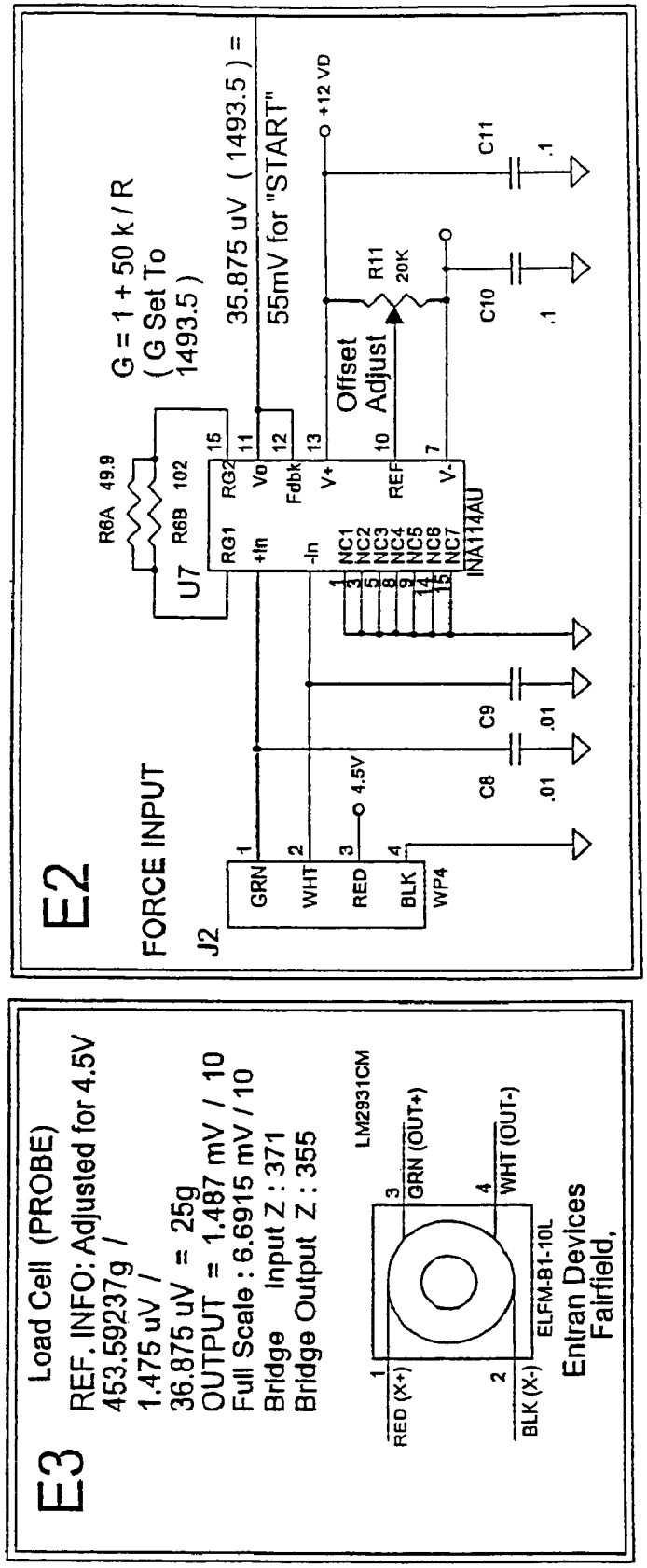
FIG. 4 is an electronic schematic of the force applicator of the present invention.
Figure 4B:
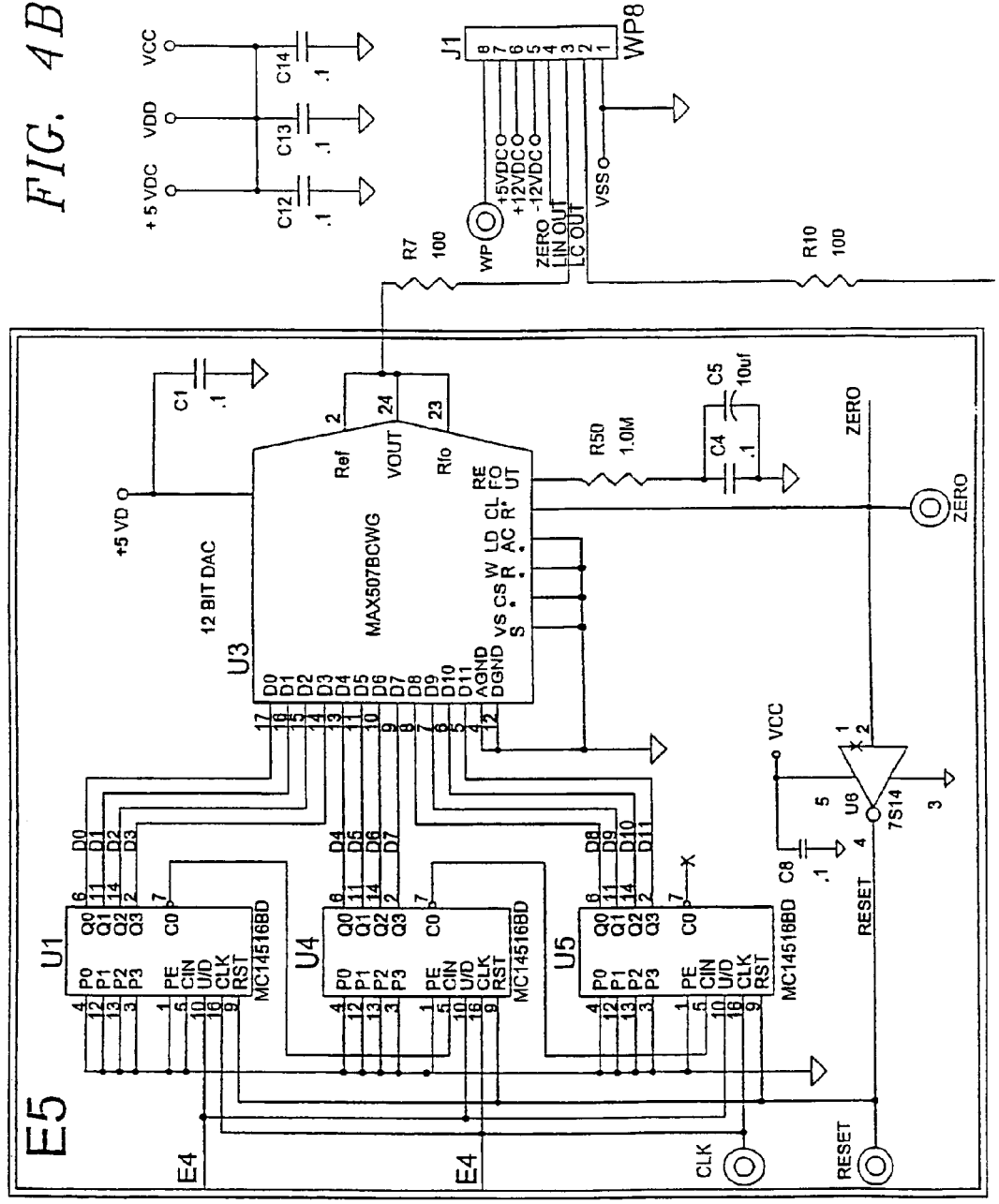

FIG. 4 circuitry E5, a "ripple counter" (12 bit up/down counter) comprised of U1, U4 and U5 increments or decrements based on the input signals from U2. This "displacement" data feeds U3, a 12-bit DAC (MAX507 Maxim Integrated Products—Sunnyvale, Calif.). U3 output signal "LIN_OUT" is then routed to connector cable J1 position 3 and then to the breakout box.

Once initiated, simultaneous pressure and distance measurements are read by the laptop computer data acquisition card (DAC-700 National Instruments—Austin, Tex.) through flex cable L1 from the breakout box.

The laptop performs the following functions: Upon detection of a start signal from circuitry B1 of the breakout box (FIG. 5), begins a three second sample of pressure and distance data; Provides the timing signal for the operator (i.e. doctor) for the duration of the data acquisition phase; Sounds an alarm when 7.5 pounds, and then 10 pounds, of pressure is detected at the load cell.

The software program (LabVIEW National Instruments—Austin, Tex.) plots and displays the points of pressure vs. distance. It also performs a mathematical analysis of the data, including a linear regression analysis based on user selected data ranges. The program is capable of saving the data and repeatedly analyzing the data for replotting and reprinting.

Figure 6:
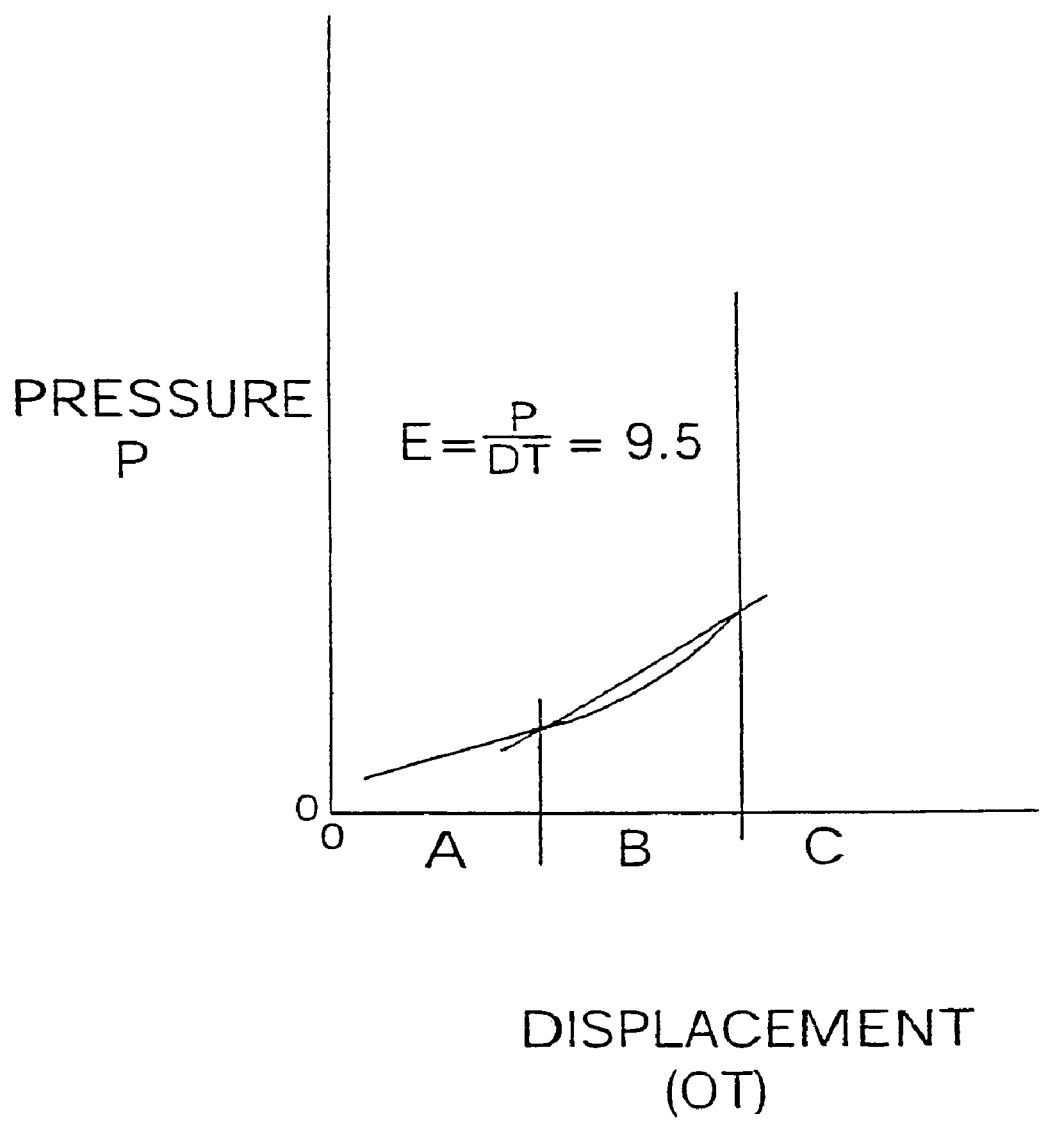
FIG. 6 is chart of displacement vs. pressure as determined by the applicator instrument.

The linear regression of a specific portion of the curve of pressure vs. distance is the hardness measurement of the compartment, note FIG. 6. The plot of the pressure to distance curve has information regarding subcutaneous fat thickness as well as muscle compartment pressure and underlying muscle tone (FIG. 6). These three parts of the curve include the beginning portion (A), mid portion (B) and end portion (C). The initial portion (A) corresponds to the subcutaneous fat portion overlying the compartment. The mid linear portion (B) corresponds to the pressure within the compartment. The end part of the curve (C) is the compaction of the muscle compartment which gives information regarding the tone of the muscle (FIG. 5). The linear regression plot (D) of mid portion (B) gives the hardness value (E) of the muscle.

Analysis of Acquired Data

The present invention further relates to the software code and arithmetic logic units employed in analyzing data gathered by the applicator instrument. This code can be written in any number of languages, such as "C," "C++", or assembly language for execution on a computer processing unit ("CPU") employing a disk storage medium. The software is designed to analyze the pressure and displacement data gathered by the applicator and make a qualitative evaluation.

The applicator instrument is first applied by the clinician to the limb suspected of compartment syndrome, whereby a number of pressure and displacement data points are acquired as noted more fully above. These data points correspond to the pressure encountered by the force probe and the distance the force probe travels into the limb, with the total distance corresponding to the total travel of the force probe into the affected region. Once these data points are acquired, they are stored within the disk storage medium for processing by the CPU and software.

Figure 7:
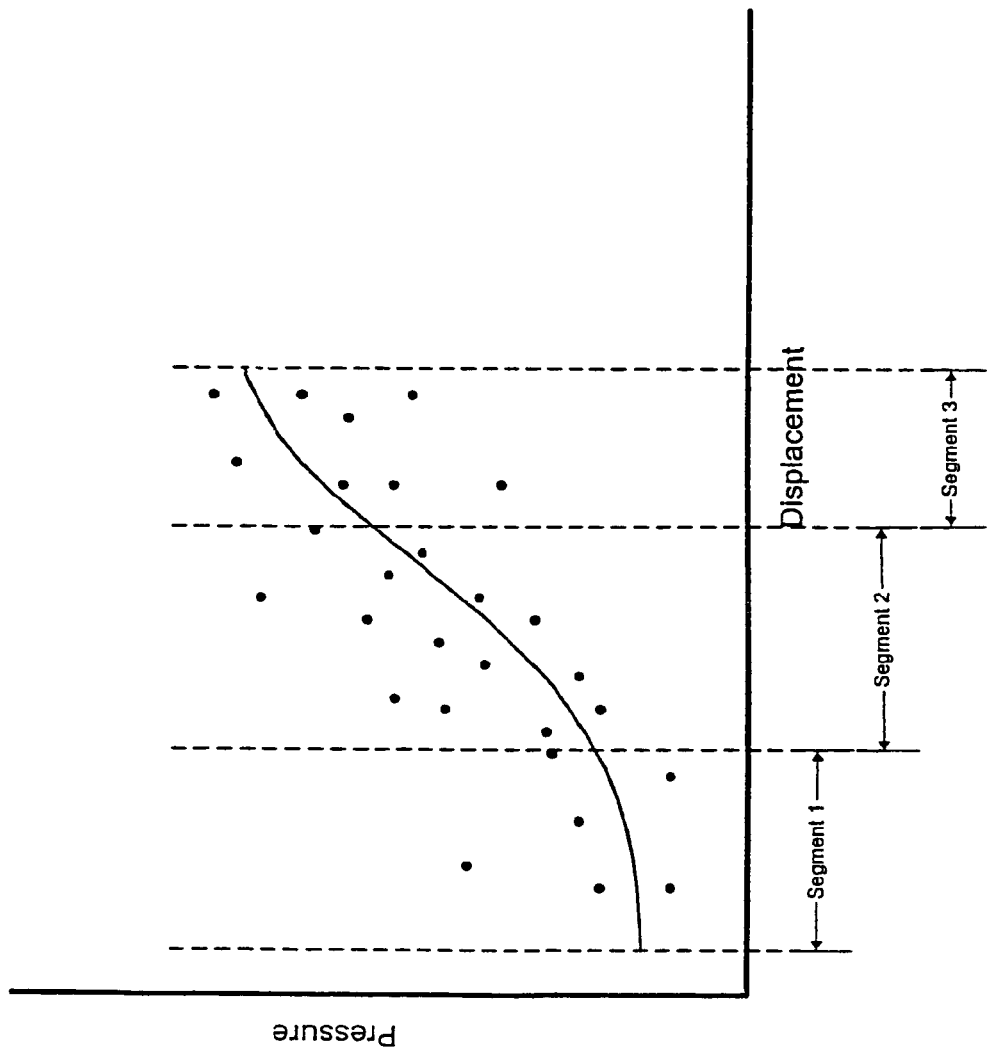
FIG. 7 is a plot of acquired displacement and pressure points and a corresponding regression curve relating displacement to pressure.

The software then uses a linear regression analysis to plot a regression curve for the stored data points. This analysis finds the best fit for all stored data points, whereby displacement is related to pressure in a two dimensional X-Y plane. The gathered data points and associated regression curve are illustrated in the graph of FIG. 7. FIG. 7 also illustrates that there are three parts to the regression curve. The first part represents the resistance encountered by the force probe as a result of the skin and subcutaneous fat in the affected region. The second segment represents the resistance encountered as a result of the muscle within the muscle compartment. The third segment represents resistance due to muscle compaction.

The regression curve is broken down into its three component segments via an iterative mean square error (MSE) analysis as described hereinafter. Specifically, the software computes an MSE value based on a number of acquired pressure data points (N) relative to the pressure predicted by the regression curve. This computation is made over a given distance interval in accordance with the following equation (equation 1):

$$MSE = \sum_{i=0}^{i=N-1} (p_i - y_i)^2 / N \qquad \text{Equation 1}$$

wherein N is the total number of selected data points, p is the pressure value predicted from the regression line, and y is the actual pressure value.

Figure 8:
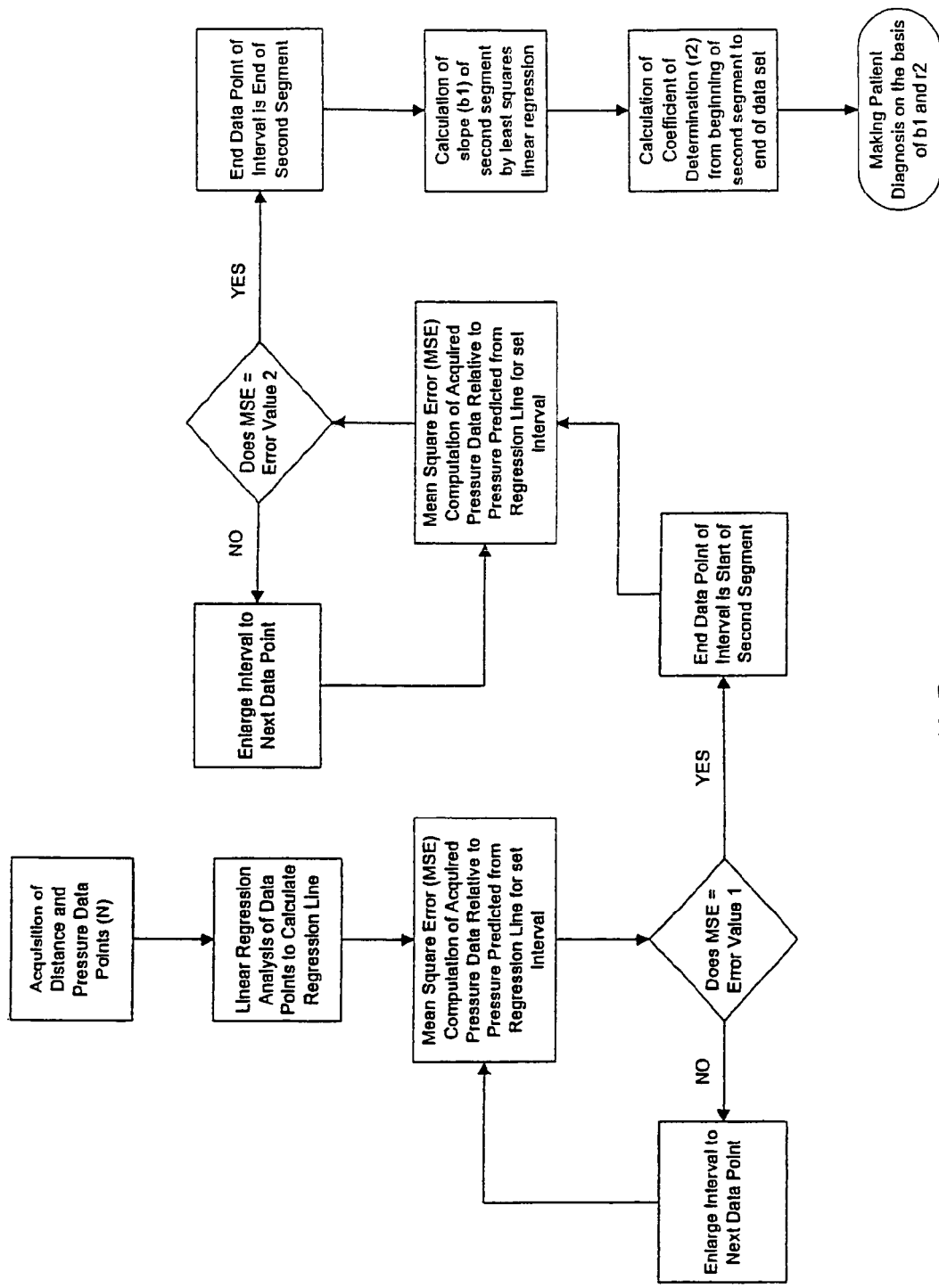
FIG. 8 is a flow chart of the software employed in the present invention.

Thereafter, the software compares the computed MSE value to a predetermined value (Value-1) that has been established by clinical muscle testing. On the basis of current clinical testing, Value-1 is equivalent to a MSE of 10. As noted in the flow chart of FIG. 8, the comparison is carried out as part of an iterative process whereby if MSE is less than Value-1, the MSE is re-computed over an increased interval with an increased number of acquired pressure data points (N). The computations are continually carried out incrementally increasing the interval (from i=0 until i=N−1) until MSE equals or exceeds Value-1. Once MSE equals or exceeds Value-1, the end of the interval is designated as the beginning of the second segment of the data curve. This designated point is then stored.

The end of the second segment is ascertained by the software in a similar iterative process. Namely, the computed MSE values are compared to a second predetermined value (Value-2), which is likewise established by clinical muscle testing. On the basis of current clinical testing, Value-2 is equivalent to a MSE of 1300. MSE is re-calculated over an increased interval if MSE is less than Value-2. Once MSE equals or exceeds Value-2, the end of the interval is designated as the end of the second segment of the data curve. The beginning and end points are then stored for future computations. The beginning and end points of the third segment are likewise determined and stored for future computation. The third segment starts at the end of the second segment and extends until the end of the regression curve, which is the end of the data acquisition.

Next, the software is employed in computing the slope of the second segment and the linearity of the second and third segments. These computations are described below in conjunction with equations 2 and 3. The slope of the second segment is correlated to hardness within the muscle compartment upon the muscle being compressed. An increased linearity of the second and third segments corresponds to increased hardness due to the muscle being further compressed by the applicator instrument. The correlated values for hardness and increased hardness are then used to make a qualitative evaluation of the affected region. These computations are described in greater detail hereinafter.

The software calculates the slope of the second segment through a least squares linear regression analysis in accordance with the following equation (equation 2):

$$b_1 = S_{xy}/S_{xx} \quad b_0 = \bar{e} - b_1 \bar{x}$$

Equation 2 where $x_i$ represents incremental displacement values along the regression curve and $y_i$ represents corresponding incremental pressure values and where $S_{xy} = \Sigma(x_i-\bar{x})(y_i-\bar{y})$ and $S_{xx} = \Sigma(x_i-\bar{x})_2$ and $\bar{y}$ and $\bar{x}$ are the sample means of the y and x observations, respectively. Additionally, $b_o$ is the constant offset of the equation: $\bar{y} = b_1\bar{x} + b_o$ The software then calculates the linearity of the second and third segments via a coefficient of determination in accordance with the following equation (equation 3):

$$R^2 = (n\Sigma x_i y_i - \Sigma x_i \Sigma y_i)^2 / ([n\Sigma x_i^2 - (\Sigma x_i)^2][n\Sigma y_i^2 - (\Sigma y_i)^2])$$

Equation 3 wherein n is the number of data points, $x_i$ represents incremental displacement values along the regression curve and $y_i$ represents corresponding incremental pressure values.

As the coefficient of determination approaches 1.0, the curve approaches perfect linearity (i.e. a straight line). This, in turn, represents increased hardness of the muscle compartment and a muscle that is at risk of compartment syndrome.

Thereafter, on the basis of the computed values for slope ($b_1$) and the coefficient of determination ($R^2$) a diagnosis can be made on a qualitative basis. This is achieved by comparing $b_1$ and $R^2$ to stored values based upon clinical muscle testing. On the basis of current clinical testing, a coefficient of determination ($R^2$) greater than or equal to 0.975 signifies compartment syndrome. Likewise, on the basis of current clinical testing, it appears that a slope value ($b_1$) that is 1.5 times greater than the slope value for an uninjured limb indicates compartment syndrome. When the computed values for $b_1$ and $R^2$ equal or exceed these stored values, the clinician knows that the muscle is exhibiting the properties of a muscle at risk for compartment syndrome.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A method of employing an applicator instrument and force probe to noninvasively evaluate the muscle compartment of a limb suspected of compartment syndrome, the method comprising the following steps:

applying the applicator instrument to the limb suspected of compartment syndrome, the applicator instrument acquiring a number of pressure and displacement data points, wherein the acquired pressure data points correspond to the pressure encountered by the force probe and the acquired displacement data points correspond to the displacement of the force probe into the limb, the total displacement corresponding to the total travel of the force probe into the limb;

plotting the acquired data points and analyzing the plotted data using linear regression to calculate a regression curve, the regression curve constituting the best fit for the plotted data points and relating displacement to pressure, the regression curve having first, second and third segments;

computing a mean square error (MSE) of acquired pressure data points relative to pressure predicted by the regression curve over a given interval;

comparing the computed MSE to a predetermined value (Value-1) and re-computing the MSE over an increased interval if the MSE is less than Value-1;

designating the start of the second segment when MSE is equal to or exceeds Value-1;

comparing MSE to a predetermined value (Value-2) and re-computing the MSE over an increased interval if the MSE is less than Value-2;

designating the end of the second segment when MSE is equal to or exceeds Value-2;

calculating the slope of the second segment through a least squares linear regression analysis, the slope corresponding to pressure within the muscle compartment;

designating the third segment of the regression curve, the third segment starting at the end of the second segment and extending until the end of the regression curve;

calculating the linearity of the second and third segments via a coefficient of determination, an increased linearity of the second and third segments corresponding to increased hardness within the muscle compartment;

making a diagnosis on the basis of the slope and linearity.

2. A method of employing an applicator instrument and force probe to noninvasively evaluate the muscle compartment of a limb suspected of compartment syndrome, the method comprising the following steps:

applying the applicator instrument to the limb suspected of compartment syndrome, the applicator instrument acquiring a number of pressure and displacement data points;

plotting the acquired data points and analyzing the plotted data using linear regression to calculate a regression curve, the regression curve constituting the best fit for the plotted data points and relating displacement to pressure, the regression curve having first, second and third segments;

computing a mean square error (MSE) of acquired pressure data points relative to pressure predicted by the regression curve over a given interval;

comparing the computed MSE to a predetermined value (Value-1) and re-computing the MSE over an increased interval if the MSE is less than Value-1;

designating the start of the second segment when MSE is equal to or exceeds Value-1;

comparing MSE to a predetermined value (Value-2) and re-computing the MSE over an increased interval if the MSE is less than Value-2;

designating the end of the second segment when MSE is equal to or exceeds Value-2;

designating the third segment of the regression curve, the third segment- starting at the end of the second segment and extending until the end of the regression curve;

making a diagnosis on the basis of the slope and linearity of the second and third segments.

3. The method of claim 2 comprising the following additional steps:

calculating the slope of the second segment through a least squares linear regression analysis, the slope corresponding to pressure within the muscle compartment;

calculating the linearity of the second and third segments via a coefficient of determination, an increased linearity of the second and third segments corresponding to increased hardness within the muscle compartment;

making a diagnosis on the basis of the slope and linearity.

4. The method of claim 2 wherein Value-1 is equal to 10.

5. The method of claim 2 wherein Value-2 is equal to 1300.

6. The method of claim 3 wherein a slope that is 1.5 times greater then the slope for an uninjured limb indicates compartment syndrome.

7. The method of claim 3 wherein a coefficient of determination that is greater than or equal to 0.975 indicates a limb with compartment syndrome.

8. A data processing system for evaluating a muscle compartment of a limb suspected of compartment syndrome, the system comprising:

a computer processing unit for processing data;

a storage medium storing a number of acquired pressure and displacement data points relative to the muscle compartment being evaluated;

an arithmetic logic circuit configured to calculate a regression curve relating displacement to pressure from the stored data points, the regression curve constituting the best fit for the stored data points and having first, second and third segments and;

an arithmetic logic circuit configured to calculate a mean square error (MSE) for acquired pressure data points relative to the regression curve over a given distance, the arithmetic logic circuit comparing the computed MSE to a predetermined value (Value-1) and re-computing the MSE over an increased distance if MSE is less than Value-1, the arithmetic logic circuit storing a value that represents the beginning of the second segment of the regression curve when MSE is equal to or exceeds Value-1, the arithmetic logic circuit further comparing MSE to a predetermined value (Value-2) and re-computing the MSE over an increased distance if the MSE is less than Value-2, the arithmetic logic circuit storing a value that represents the end of the second segment of the regression curve when MSE is equal to or exceeds Value-2;

an arithmetic logic circuit configured to calculate the slope of the second segment through a least squares linear regression analysis, the slope corresponding to the hardness of a muscle within the muscle compartment when it is compressed;

an arithmetic logic circuit configured to calculate the linearity of the second and third segments of the regression curve via a coefficient of determination, the linearity corresponding to the hardness of a muscle within the muscle compartment as it becomes progressively compacted.

9. A data processing system for evaluating a muscle compartment of a limb suspected of compartment syndrome, the system comprising:

a computer processing unit for processing data;

a storage medium storing a number of acquired pressure and displacement data points relative to the muscle compartment being evaluated;

an arithmetic logic circuit configured to calculate a regression curve relating displacement to pressure from the stored data points, the regression curve constituting the best fit for the stored data points and having first, second and third segments and;

an arithmetic logic circuit configured to calculate a mean square error (MSE) for acquired pressure data points relative to the regression curve over a given distance, the arithmetic logic circuit comparing the computed MSE to a predetermined value (Value-1) and re-computing the MSE over an increased distance if MSE is less than Value-1, the arithmetic logic circuit storing a value that represents the beginning of the second segment of the regression curve when MSE is equal to or exceeds Value-1, the arithmetic logic circuit further comparing MSE to a predetermined value (Value-2) and re-computing the MSE over an increased distance if the MSE is less than Value-2, the arithmetic logic circuit storing a value that represents the end of the second segment of the regression curve when MSE is equal to or exceeds Value-2;

an arithmetic logic circuit configured to calculate the slope of the second segment through a least squares linear regression analysis, the slope corresponding to the hardness of a muscle within the muscle compartment when it is compressed.

10. The data processing system as described in claim 9 further comprising:

an arithmetic logic circuit configured to calculate the linearity of the second and third segments of the regression curve via a coefficient of determination, the linearity corresponding to the hardness of a muscle within the muscle compartment as it becomes progressively compacted.

* * * * *

UNITED STATES PATENT AND TRADEMARK OFFICE
CERTIFICATE OF CORRECTION

PATENT NO.       : 7,232,415 B2
APPLICATION NO.  : 11/453292
DATED            : June 19, 2007
INVENTOR(S)      : Bruce Steinberg Page 1 of 1

It is certified that error appears in the above-identified patent and that said Letters Patent is hereby corrected as shown below:

Column 9, Line 6 Equation 2 should read as follows:

$$b_1 = S_{xy}/S_{xx} \quad b_0 = \bar{y} - b_1 \bar{x}$$

Signed and Sealed this

Third Day of June, 2008

JON W. DUDAS
*Director of the United States Patent and Trademark Office*